United States Patent [19]

Bednar et al.

[11] Patent Number: 5,753,702
[45] Date of Patent: May 19, 1998

[54] ARACHIDONIC ACID METABOLITE, 16-HETE

[75] Inventors: Martin M. Bednar; Cordell E. Gross, both of South Burlington, Vt.; Michael Balazy, Courtland Manor, N.Y.; John R. Falck, University Park, Tex.

[73] Assignee: University of Vermont, Burlington, Vt.

[21] Appl. No.: 652,327

[22] Filed: May 22, 1996

[51] Int. Cl.$^6$ .................................................. A61K 31/23
[52] U.S. Cl. ............................................................ 514/552
[58] Field of Search .............................................. 514/552

[56] References Cited

U.S. PATENT DOCUMENTS 5,256,538  10/1993  Aiken et al. .

OTHER PUBLICATIONS

Chemical Abstracts AN 1995:138771, Takada et al.
Chemical Abstracts AN 1990:493392, Falck et al.
Chemical Abstracts AN 1994:474474, Knickle et al.
Falck, J.R. et al., The Journal of Biological Chemistry, vol. 265 (18):10244–10249 (1990).
Heckmann, B. et al. . Tetrahadron Letters, vol. 37(9):1425–1428 (1996).
Bednar, M.M. et al.. Abstract from meeting held in Florence, Italy (Jun. 1994).
Ying Zhu et al., Hypertension, vol. 25 (4).Part 2:854–859 (Apr. 1995).
Gross, C.E. et al. . Neurological Res. , vol. 16:465–470 (Dec. 1994).
Lesch, M.E. et al. . Agents and Actions. vol. 34:25–27 (1991).
Lee, T.H. et al. . The New England Journal of Medicine. vol. 312(19):1217–1224 (5/9/85).
Hill, E. et al. . Biological Mass Spectrometry, vol. 21:249–253 (1992).
Watanabe, Masako et al. , Br. J. Pharmacol. 102:239–245 (1991).
Laethem, R.M. et al. , the Journal of Biological Chemistry, vol. 268(17):12912–12918 (1993).
Balazy, M., The Journal of Biological Chemistry, vol. 266(35):23561–23567 (1991).
Bednar, M.M. et al., Journal of Thrombosis and Thrombolysis:1:179–185 (1995).
Springer, T.A. , Annu. Rev. Cell Biol. , 6:359–402 (1990).
Kraemer, R. et al. , American Journal of Pathology, vol. 128(3):446–454 (1987).
Hatzelmann A. et al. , Euro. J. Biochem. 173:445–452 (1988).

*Primary Examiner*—Keith MacMillan
*Attorney, Agent, or Firm*—Wolf, Greenfield & Sacks, P.C.

[57] ABSTRACT

The present invention provides methods and products for inhibiting neutrophil adhesion and neutrophil aggregation. The invention includes a method for treating a subject to inhibit neutrophil adhesion and neutrophil aggregation by administering 16-hydroxyeicosatetraenoic acid (16-HETE) to the subject. 16-HETE is an arachidonic acid metabolite. The invention also includes a pharmaceutical preparation of 16-HETE.

44 Claims, 2 Drawing Sheets

ARACHIDONIC ACID METABOLITE, 16-HETE

BACKGROUND OF THE INVENTION

The inflammatory response is an important element of a host's natural defense mechanism against pathogens. It also is involved in wound healing. Despite the central beneficial role that the inflammatory response plays in host survival, it also can have a damaging effect in states of inflammation.

Leukocytes, which are the major cellular components of inflammatory and immune responses, encompass a broad class of cells including neutrophils, lymphocytes, monocytes, eosinophils, and basophils. Neutrophils, which play a key role in the inflammatory response, are generally present within the body in a resting unstimulated state. Once stimulated, the neutrophils migrate to the site of injury and release toxic factors.

The migratory capability of a neutrophil is dependent on the ability of the neutrophil to alter its adhesive properties. In a resting unstimulated state a neutrophil is not adhesive and cannot migrate. Once the neutrophil has been stimulated, however, it becomes more adhesive and is capable of migrating. The increase in neutrophil adhesiveness causes the stimulated neutrophil to aggregate and to adhere to endothelium. Stimulation of the neutrophil also causes the neutrophil to undergo diapedesis, which involves the migration of the neutrophil between post-capillary endothelial cells into the tissues.

In the tissues, an activated neutrophil releases enzymes such as collagenase and elastase, among others. Neutrophil stimulation may also initiate a burst of oxygen consumption, with concomminant activation of the hexose-monophosphate shunt and activation of nicotinamide-adenine dinucleotide phosphate (NADPH) oxidase. Activation of these systems results in the formation and release of factors such as hydrogen peroxide and hydroxyl radicals, which are toxic to microorganisms and tumor cells and thereby facilitating the destruction of the injury causing agent.

Several studies have focused on analyzing the control and regulation of the adhesive properties of neutrophils. Much of this research has centered on adhesion receptors and also on metabolites of arachidonic acid, C20 carbon fatty acid found in every cell membrane. Arachidonic acid metabolism occurs by different mechanisms in stimulated versus unstimulated neutrophils and results in the production of a different spectrum of metabolites in stimulated versus unstimulated neutrophils.

In stimulated neutrophils, the cytochrome P450 mixed function oxidase system appears to be more active. Moreover, during neutrophil stimulation, 5-lipoxygenase is translocated to the membrane compartment fraction, where it produces 5-hydroperoxyeicosatetraenoic acid (5-HPETE). 5-HPETE is then either metabolized to 5-hydroxyeicosatetraenoic acid (5-HETE) by peroxidase or dehydrated to form leukotriene $A_4$. Leukotriene $A_4$ is converted into leukotriene $B_4$ which is a potent chemotactic agent and promoter of neutrophil adhesion.

In unstimulated neutrophils, the metabolism of arachidonic acid is markedly different than that in stimulated neutrophils. The metabolism of arachidonic acid in unstimulated neutrophils is sensitive to cytochrome P450 inhibitors but not to cyclooxygenase or lipoxygenase inhibitors. Hatzelmann and Ullrich characterized the metabolites produced in unstimulated neutrophils, reporting the finding that arachidonic acid is metabolized to 20-HETE and 15-HETE. Hatzelmann, Eur. J. Biochem. 173, 445–452 (1988). Another study, Kraemer et al., found that the arachidonic acid metabolic products formed in unstimulated neutrophils exhibited a potent anti-aggregatory activity toward human neutrophils, suggesting that the identified arachidonic acid metabolites may play some role in the regulation of neutrophil adhesion and aggregation properties. Kraemer et al., Am. J. Pathol. 128, 446–454 (1987).

SUMMARY OF THE INVENTION

Several diseases or conditions are characterized by excessive inflammation associated with neutrophil adhesion and neutrophil aggregation. The present invention provides methods and products for inhibiting neutrophil adhesion and neutrophil aggregation. It has been discovered that 16-HETE (16-hydroxyeicosatetraenoic acid) is a component of arachidonic acid metabolism in neutrophils and that 16-HETE is a potent inhibitor of neutrophil adhesion and neutrophil aggregation. Although 16-HETE has been identified as a component of arachidonic acid metabolism in platelets, it has not previously been identified as a component of neutrophils. Likewise, the biological effects of 16-HETE on neutrophils have not been previously reported.

One aspect of the invention is directed to a method for inhibiting neutrophil adhesion and neutrophil aggregation. The method involves contacting neutrophils with 16-HETE in situ in an amount effective to inhibit neutrophil adhesion and neutrophil aggregation. This aspect of the invention may be applied in vitro or in vivo to inhibit neutrophil adhesion and neutrophil aggregation at a desired time.

According to another aspect of the invention, a method for treating a subject to inhibit neutrophil adhesion or neutrophil aggregation is provided. A composition of 16-HETE is administered to a subject having an adverse medical condition mediated by neutrophil adhesion and/or neutrophil aggregation in an amount effective to inhibit the neutrophil adhesion or neutrophil aggregation. In one embodiment of the invention an adverse medical condition mediated by neutrophil adhesion and/or neutrophil aggregation is an inflammatory disease or condition. According to particular embodiments, the inflammation is characteristic of or results from meningitis, cerebral edema, arthritis, nephritis, adult respiratory distress syndrome, pancreatitis, myositis, neuritis, connective tissue diseases, phlebitis, arteritis, vasculitis, allergy, anaphylaxis, gout, ehrlichiosis, organ transplants, stroke, myocardial infarction and/or ulcerative colitis.

According to another aspect of the invention the 16-HETE may be administered to a subject in conjunction with other drugs for treating an adverse medical condition mediated by neutrophil adhesion and/or neutrophil aggregation. In one embodiment of the invention the 16-HETE may be administered to the subject in conjunction with other drugs for treating an inflammatory disease or condition. According to another embodiment, the 16-HETE may be administered to the subject in conjunction with other drugs for treating an ischemic disease or condition. In one embodiment the 16-HETE is administered to a subject having an ischemic disease or condition, in conjunction with a thrombolytic agent.

According to another aspect of the invention, pharmaceutical preparations are provided. These pharmaceutical preparations include the 16-HETE of the invention together with a pharmaceutically acceptable carrier. The 16-HETE is present in a therapeutically effective amount for treating the adverse medical condition mediated by neutrophil adhesion and/or neutrophil aggregation. Preferably the 16-HETE is 16(R)-HETE.

Preferably the 16-HETE is 16(R)-HETE. Most preferably the 16(R)-HETE is isolated 16(R)-HETE.

In an embodiment, the pharmaceutical preparation of the invention includes other therapeutic agents for treating the adverse medical condition mediated by neutrophil adhesion and/or neutrophil aggregation. In one embodiment of the invention the pharmaceutical preparation includes other therapeutic agents for treating an inflammatory disease or condition. According to particular embodiments the therapeutic agent for treating the inflammatory disease or condition is selected from the group consisting of antibiotics, such as tetracycline antibiotics, aminoglysodes, macrolides, lincomycins, penicillanic acid (6-APA)- derivatives having 6β-acylamino groups, cephalosporanic acid (7-ACA)- derivatives having 7β-acylamino groups, penicillanic acid, β-lactam antibiotics of the clavam, penem and carbapenen type, and antibiotics of the bicozamycin, novobiocin, chloramphenicol or thiamphenicol, rifampicin, fosfomycin, colistin and vancomycin and antiphlogistics, such as glucocorticoids, immunosuppressive agents, penicillamine, hydroxychloroquine, and nonsteroidal inflammation-inhibitors. According to another embodiment, the pharmaceutical preparation includes other therapeutic agents for treating ischemic disease or condition. According to particular embodiments the therapeutic agent is selected from the group consisting of: anticoagulation agents, such as heparin, warfarin, coumadin, dicumarol, phenprocoumon, acenocoumarol, ethyl biscoumacetate, and indandione derivatives; antiplatelet agents, such as aspirin, thienopyridine, dipyridamole and sulfinpyrazone; and thrombolytic agents, such as plasminogen, $\alpha_2$-antiplasmin, streptokinase, antistreplase, tissue plasminogen activator, and urokinase. According to one important embodiment of the invention, the pharmaceutical preparation includes the 16-HETE of the invention together with a thrombolytic agent.

In one embodiment of the invention, the pharmaceutical preparations contain 16-HETE as a substantially pure preparation of isolated 16-HETE. The 16-HETE may be isolated from a biological preparation or may be a chemically synthesized preparation of 16-HETE. According to yet another embodiment, the 16-HETE is selected from the group consisting of 16(R)-HETE and 16(S)-HETE. Preferably, the 16-HETE is isolated 16(R)-HETE.

According to another aspect of the invention, pharmaceutical preparations of the invention consist essentially of 16(R)-HETE.

The invention also provides a composition of 16-HETE for use as a medicament.

The invention also provides a composition of 16-HETE for use in the manufacture of a medicament for the treatment of adverse medical conditions mediated by neutrophil adhesion and/or neutrophil aggregation. In another embodiment the invention provides a composition of 16-HETE for use in the manufacture of a medicament for the treatment of an inflammatory disease or condition. In another embodiment the invention provides a composition of 16-HETE for use in the manufacture of a medicament for the treatment of an ischemic disease or condition, including but not limited to, stroke.

These and other aspects of the invention, as well as various advantages and utilities, will be more apparent with reference to the detailed description of the preferred embodiments.

BRIEF DESCRIPTION OF THE DRAWINGS

The present invention may be more easily and completely understood when taken in conjunction with the accompanying drawings, in which.

DETAILED DESCRIPTION OF THE INVENTION

Figure 1:
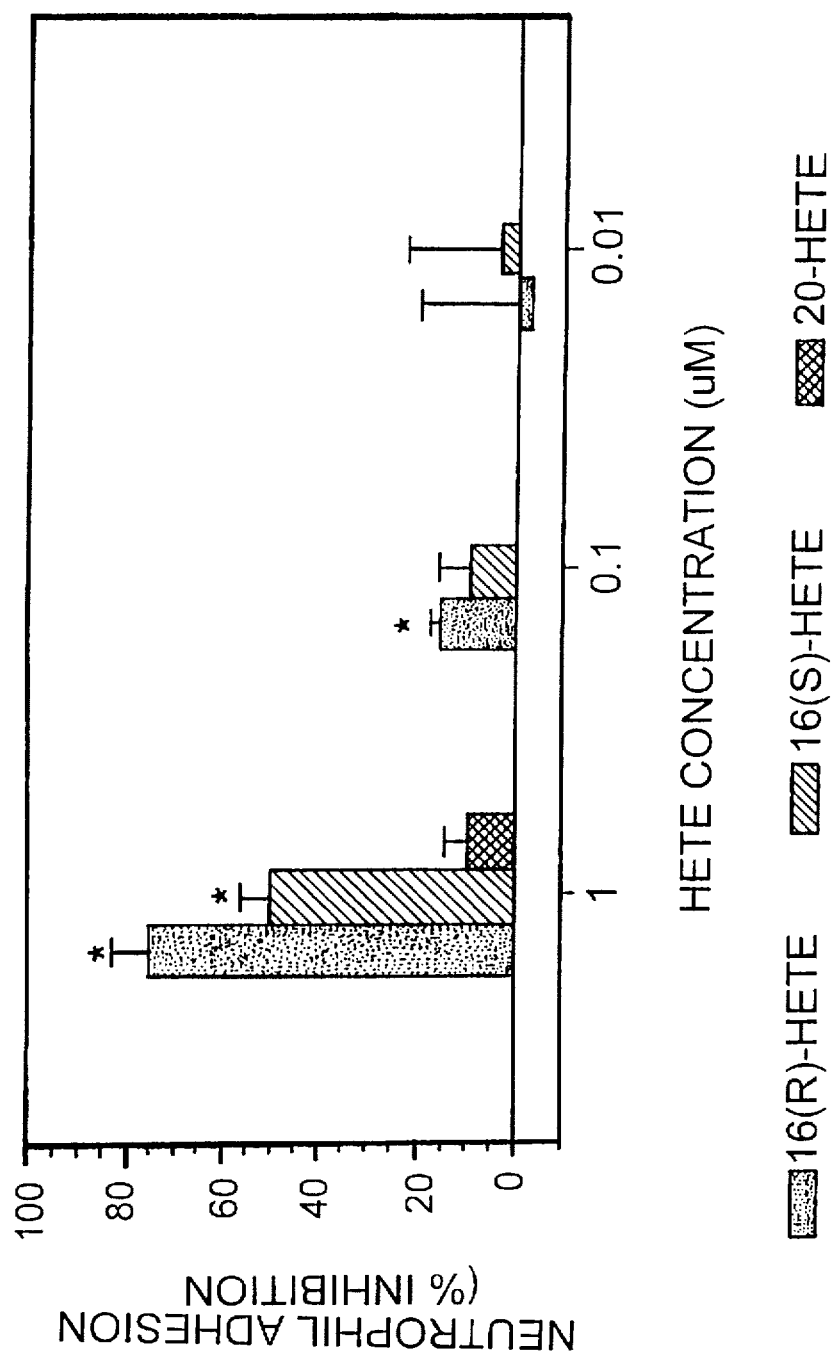
FIG. 1 is a bar graph depicting the percent inhibition of neutrophil adhesion to a gelatin matrix resulting from a 10 minute pre-incubation with 16(R)-HETE, 16(S)-HETE, and 20-HETE on basil human neutrophils.

The invention involves the finding that an arachidonic acid metabolic product is effective in inhibiting neutrophil adhesion and neutrophil aggregation. Applicants have discovered that the compound 16-HETE, can be used effectively to inhibit neutrophil adhesion and neutrophil aggregation in both stimulated and unstimulated neutrophils.

Although 16-HETE has been identified as an arachidonic acid metabolic product in platelets, it was never before identified in neutrophils. Several studies have examined the arachidonic acid metabolic products produced by neutrophils but have not identified 16-HETE. Hatzelmann and Ullrich reported that arachidonic acid is metabolized to 20-HETE and 15-HETE in human neutrophils (Hatzelmann, supra) and Hill and Murphy demonstrated that stimulation of human neutrophils produced 20-HETE. Hill, *Biol. Mass. Spectrum* 21, 249–253 (1992).

Applicants have discovered that 16-HETE is a metabolic product of arachidonic acid in unstimulated human neutrophils and that 16-HETE is capable of inhibiting neutrophil adhesion. Although Hatzelmann as well as other groups have characterized the metabolites of arachidonic acid in unstimulated neutrophils, 16-HETE was not identified. It was surprising to find that 16-HETE was a component of arachidonic acid metabolism. The reason that others did not previously identify 16-HETE is probably due to the similar chromatographic mobility of 20-HETE and 16-HETE during reverse phase HPLC (which is a commonly used procedure for separating metabolites).

Furthermore, the biological effects of 16-HETE on human neutrophils has not been reported previously. Applicants have discovered that 16-HETE is a potent inhibitor of both unstimulated and stimulated neutrophils. As demonstrated in the example section, 16-HETE is capable of inhibiting basal and thrombin-stimulated neutrophil adhesion, and fMLP-induced neutrophil aggregation. 16-HETE may be used to inhibit unwanted neutrophil adhesion and aggregation by treating neutrophils that have been stimulated either in vivo or in vitro.

The present invention thus involves methods and products for inhibiting neutrophil adhesion and neutrophil aggregation. According to one aspect of the invention, the method involves administering 16-HETE to neutrophils in situ in an amount effective to inhibit neutrophil aggregation and neutrophil adhesion. By definition, the word "in-situ" encompasses and includes the terms "in-vivo", "ex-vivo" and "in-vitro."

16-HETE has the following structural formula:

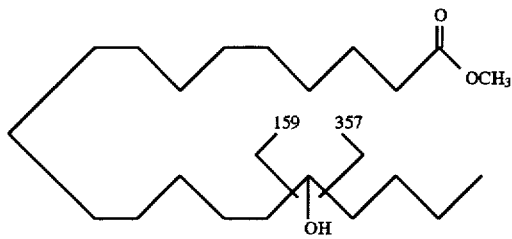

16-HETE is administered in an effective amount. An effective amount is one which inhibits to any degree neutrophil adhesion and neutrophil aggregation. An effective amount may be determined using the assay described in Example 3 infra for neutrophil adhesion. Effective amounts will depend, of course, on the particular condition being treated; the severity of the condition; individual patient parameters including age, physical condition, size and weight; concurrent treatment, frequency of treatment; and the mode of administration. These factors are well known to those of ordinary skill in the art and can be addressed with no more than routine experimentation. It is preferred generally that a maximum dose be used, that is, the highest safe dose according to sound medical judgment, particularly if acute stroke is the dominant clinical manifestation.

The invention includes a method for treating a subject to inhibit neutrophil adhesion or neutrophil aggregation by administering 16-HETE to a subject having an adverse medical condition mediated by neutrophil adhesion and/or neutrophil aggregation. In one embodiment a subject having an adverse medical condition mediated by neutrophil adhesion and/or neutrophil aggregation is one who has an inflammatory disease or is at risk of developing an inflammatory disease. In another embodiment a subject having an adverse medical condition mediated by neutrophil adhesion and/or neutrophil aggregation is one who has an ischemic disease.

A "subject" as used herein includes humans, non-human primates, dogs, cats, horses, sheep, goats, cows, rabbits, pigs and rodents.

Both inflammatory diseases and ischemic diseases are characterized by inflammation associated with neutrophil adhesion and neutrophil aggregation due to excessive neutrophil stimulation. While not intending to be bound by any particular theory, it is believed that excessive stimulation of neutrophils causes the neutrophils to migrate to the site of injury, where they release toxic factors and damage surrounding tissue.

An "inflammatory disease or condition" as used herein refers to any condition characterized by local inflammation at a site of injury or infection and includes autoimmune diseases, certain forms of infectious inflammatory states, undesirable neutrophil activity characteristic of organ transplants or other implants and virtually any other condition characterized by unwanted neutrophil activation. These conditions include but are not limited to meningitis, cerebral edema, arthritis, nephritis, adult respiratory distress syndrome, pancreatitis, myositis, neuritis, connective tissue diseases, phlebitis, arteritis, vasculitis, allergy, anaphylaxis, ehrlichiosis, gout, organ transplants and/or ulcerative colitis.

An "ischemic disease or condition" as used herein refers to a condition characterized by local inflammation resulting from an interruption in the blood supply to a tissue due to a blockage or hemorrhage of the blood vessel responsible for supplying blood to the tissue such as is seen for myocardial or cerebral infarction. A cerebral ischemic attack or cerebral ischemia is a form of ischemic condition in which the blood supply to the brain is blocked. Cerebral ischemia may result in either transient or permanent deficits. The methods of the invention are particularly preferred for cerebral ischemia. A transient ischemic attack is one in which the blood flow to the brain is interrupted only briefly and causes temporary neurological deficits, which often are clear in less than 24 hours. Permanent cerebral ischemic attacks, also called stroke, are caused by a longer interruption in blood flow to the brain resulting from either a thromboembolism or hemorrhage. Thromboembolic stroke is due to the occlusion of an extracranial or intracranial blood vessel by a thrombus or embolus. Hemorrhagic stroke is caused by the rupture of a blood vessel in a subarachnoid space or intracerebral tissue.

The present invention includes a pharmaceutical composition having a therapeutically effective amount of 16-HETE included in a pharmaceutically acceptable carrier. The term "pharmaceutically acceptable carrier" as used herein means one or more compatible solid or liquid filler, dilutants or encapsulating substances which are suitable for administration to a human or other animal. The term "carrier" denotes an organic or inorganic ingredient, natural or synthetic, with which the active ingredient is combined to facilitate the application. The components of the pharmaceutical compositions also are capable of being commingled with the molecules of the present invention, and with each other, in a manner such that there is no interaction which would substantially impair the desired pharmaceutical efficacy.

The pharmaceutical preparation of the invention includes 16-HETE and a pharmaceutically acceptable carrier. In one embodiment of the invention the 16-HETE is a substantially pure preparation of isolated 16-HETE. As used herein the term "substantially pure" means that the 16-HETE is essentially free of other substances with which it may be found in natural or in vivo systems to an extent practical and appropriate for its intended use. In particular, the 16-HETE is sufficiently pure and is sufficiently free from other biological constituents so as to be useful in, for example, a pharmaceutical preparation. Because a substantially purified 16-HETE of the invention may be admixed with a pharmaceutically acceptable carrier in a pharmaceutical preparation, the 16-HETE may comprise only a small percentage by weight of the preparation. Typically the preparation of 16-HETE that has been isolated from cells or tissue includes less than 10% impurities. The 16-HETE is nonetheless substantially pure in that it has been substantially separated from the substances with which it may be associated in living systems.

As used herein the term "isolated 16-HETE" means a preparation of 16-HETE that is substantially free of HETE molecules other than 16-HETE.

As used herein the term "isolated 16-(R)-HETE" means a preparation of 16-(R)-HETE that is substantially free of HETE molecules, including 16-(S)-HETE, other than 16-(R)-HETE.

According to another embodiment, the 16-HETE is a synthetic preparation of 16-HETE. As used herein "a synthetic preparation of 16-HETE" includes a preparation of 16-HETE that is chemically derived. The chemically derived 16-HETE may be made by any chemical procedure known in the art. An example of a procedure used to synthesize 16-HETE is provided in Example 3.

According to yet another embodiment, the 16-HETE is selected from the group consisting of 16(R)-HETE and 16(S)-HETE. As used herein "16(R)-HETE" is the R-stereoisomer of 16-hydroxyeicosatetraenoic acid. As used herein "16(S)-HETE" is the S-stereoisomer of 16-hydroxyeicosatetraenoic acid. Preferably the 16-HETE is substantially pure 16(R)-HETE.

According to another embodiment the pharmaceutical preparation of the invention is a preparation consisting essentially of 16(R)-HETE.

The pharmaceutical preparation of 16-HETE may be used alone or in combination with a therapeutic agent for treating an inflammatory disease or condition. Known therapeutics are described in medical textbooks such as Harrisons, Principles of Internal Medicine (McGraw Hill, Inc., New York). The particular therapeutic used depends on the nature of the disease or condition being treated.

Therapeutics useful in the treatment of inflammatory diseases or conditions involving infectious agents include various antipathogen agents, i.e., antibiotics, antivirals, antifungals and antiparasitics. The type and concentration of therapeutic depends inter alia on the infectious agent causing the inflammatory disease or condition. For example, chloramphenicol is therapeutically useful for the treatment of meningitis due to *Streptococcus pneumoniae, Haemophilus influenzae,* and *Neisseria meningitides* but not in the treatment of meningitis due to *E. Coli* or *Klebsiella pneumoniae.* Cefotaxime, ceftizoxime, ceftriaxone, ceftazidime, and moxalactam are useful in treating all forms of meningitis. Penicillin may also be used to treat *S. pneumoniae* and *N. meningitides.*

In general, therapeutics from the group comprising antibiotics include, for example, tetracycline antibiotics, such as chlortetracycline, oxytetracycline, tetracycline, demethylchlortetracycline, metacycline, doxycycline, minocycline and rolitetracycline; aminoglysodes, such as kanamycin, amikacin, gentamicin $C_{1a}$, $C_2$, $C_{2b}$ or $C_1$, sisomicin, netilmicin, spectinomycin, streptomycin, tobramycin, neomycin B, dibekacin and kanendomycin; macrolides, such as maridomycin and erythromycin; lincomycins, such as clindamycine and lincomycin; penicillanic acid (6-APA)- and cephalosporanic acid (7-ACA)- derivatives having (6β- or 7β-acylamino groups, respectively, which are present in fermentatively, semi-synthetically or totally synthetically obtainable 6β-acylaminopenicillanic acid or 7β-acylaminocephalosporanic acid derivatives and/or 7β-acylaminocephalosporanic acid derivatives that are modified in the 3-position, such as penicillanic acid derivatives that have become known under the names penicillin G or V, such as phenethicillin, propicillin, nafcillin, oxycillin, cloxacillin, dicloxacillin, flucloxacillin, cyclacillin, epicillin, mecillinam, methicillin, azlocillin, sulbenicillin, ticarcillin, mezlocillin, piperacillin, carindacillin, azidocillin or ciclacillin, and cephalosporin derivatives that have become known under the names cefaclor, cefuroxime, cefazlur, cephacetrile, cefazolin, cephalexin, cefadroxil, cephaloglycin, cefoxitin, cephaloridine, cefsulodin, cefotiam, ceftazidine, cefonicid, cefotaxime, cefmenoxime, ceftizoxime, cephalothin, cephradine, cefamandol, cephanone, cephapirin, cefroxadin, cefatrizine, cefazedone, ceftrixon and ceforanid; and other β-lactam antibiotics of the clavam, penem and carbapenen type, such as moxalactam, clavulanic acid, nocardicine A, sulbactam, aztreonam and thienamycin; and antibiotics of the bicozamycin, novobiocin, chloramphenicol or thiamphenicol, rifampicin, fosfomycin, colistin and vancomycin Anti-virals include Zidovudine (AZT-Retrovir), Zalcitabine (Hivid-ddC), Dicanosine (Videx-ddI), Protease inhibitors of retroviruses, integrase inhibitors of retroviruses and others well known to those skilled in the art.

Other therapeutics useful in the treatment of inflammatory diseases or conditions include, but are not limited to, anti-inflammatory agents, or antiphlogistics. Antiphlogistics are, for example, glucocorticoids, such as, cortisone, hydrocortisone, prednisone, prednisolone, fluorcortolone, triamcinolone, methylprednisolone, prednylidene, paramethasone, dexamethasone, betamethasone, beclomethasone, fluprednylidene, desoxymethasone, fluocinolone, flumethasone, diflucortolone, clocortolone, clobetasol and fluocortin butyl ester; immunosuppressive agents; penicillamine; hydroxychloroquine; and nonsteroidal inflammation-inhibitors (NSAID) which encompass anti-inflammatory, analgesic, and antipyretic drugs such as salicyclic acid, difunisal and from the group comprising substituted phenylacetic acid salts or 2phenylpropionic acid salts, such as alclofenac, ibufenac, ibuprofen, clindanac, fenclorac, ketoprofen, fenoprofen, indoprofen, fenclofenac, diclofenac, flurbiprofen, pirprofen, naproxen, benoxaprofen, carprofen and cicloprofen; oxicam derivatives, such as piroxicam; anthranilic acid derivatives, such as mefenamic acid, flufenamic acid, tolfenamic acid and meclofenamic acid; anilino-substituted nicotinic acid derivatives, such as the fenamates miflumic acid, clonixin and flunixin; heteroarylacetic acids wherein heteroaryl is a 2-indol-3-yl or pyrrol-2-yl group, such as indomethacin, oxmetacin, intrazol, acemetazin, cinmetacin, zomepirac, tolmetin, colpirac and tiaprofenic acid; idenylacetic acid of the sulindac type; analgesically active heteroaryloxyacetic acids, such as benzadac; phenylbutazone; etodolac; and nabumetone.

Other therapeutics useful in the treatment of inflammatory diseases or conditions include antioxidants. Antioxidants may be natural or synthetic. Antioxidants are, for example, superoxide dismutase (SUD), 21 aminosteroids/aminochromans, vitamin C or E, etc. Many other antioxidants are well known to those of skill in the art.

The pharmaceutical preparation of 16-HETE also may be used alone or in combination with a therapeutic agent for treating an ischemic disease or condition. Therapeutics for treating ischemic diseases or conditions are described in medical textbooks such as Harrisons, Principles of Internal Medicine (McGraw Hill, Inc., New York ). The particular therapeutic used depends on the nature of the disease or condition. Examples of therapeutics useful in the treatment of ischemic diseases or conditions include anticoagulation agents, antiplatelet agents, and thrombolytic agents.

Anticoagulation agents prevent the coagulation of blood components and thus prevent clot formation. Anticoagulants include, but are not limited to, heparin, warfarin, coumadin, dicumarol, phenprocoumon, acenocoumarol, ethyl biscoumacetate, and indandione derivatives.

Antiplatelet agents inhibit platelet aggregation and are often used to prevent thromboembolic stroke in patients who have experienced a transient ischemic attack or stroke. Antiplatelet agents include, but are not limited to, aspirin, thienopyridine derivatives such as ticlopodine and clopidogrel, dipyridamole and sulfinpyrazone, as well as RGD mimetics and also antithrombin agents such as, but not limited to, hirudin.

Thrombolytic agents lyse clots which cause the thromboembolic stroke. Thrombolytic agents are well known in the art and include, but are not limited to, plasminogen, $\alpha_2$-antiplasmin, streptokinase, antistreplase, tissue plasminogen activator (t-PA), urokinase, and modified t-PA such as fibrolase. Modified t-PA includes, but is not limited to, variants having deleted or substituted amino acids or domains, variants conjugated to other molecules, and variants having modified glycosylation. Several preferred modified t-PAs have been described in PCT Publication No. W093/24635; EP 352,119; EP382174; and Suzuki et al., *J. Cardiovasc. Pharmacal.* 22, 834–840 (1993). Each of these references is hereby incorporated by reference.

Briefly, PCT Publication No. W093/24635 discloses t-PA variants having an extra glycosylation site at any of the amino acid positions 103–105 and the native glycosylation site removed at position 117 of the native human t-PA. The amino acid number refers to the amino acid in that position of the mature, wild-type t-PA polypeptide as disclosed in U.S. Pat. No. 4,766,075. These variants have extended circulatory half lives and exhibit substantially the same or improved fibrin binding affinity and fibrinolytic potency as compared to wild-type human t-PA. The disclosed variants may also include at least one amino acid substituted in the 296–299 position with alanine and/or a substitution of the amino acids at positions 274–277 of wild type t-PA (phenylalanine, arginine, isoleucine, lysine) with leucine, histidine, serine, and threonine, respectively. One particularly effective type of variant disclosed in the reference is a triple mutant variant of wild type t-PA. The first mutation in a triple mutant is the addition of one glycosylation site at least one of the amino acid positions 103–105 by e.g., substituting the native amino acid sequence 103 with an asparagine as part of an Asn-X-Ser or Asn-X-Thr tripeptidyl sequence, wherein X is any amino acid except proline. The second mutation involves the removal of a glycosylation site at native amino acid site 117 (Asn) and replacing it with another amino acid, preferably glutamine. The third mutation is the replacement of native amino acids 296–302 with other amino acids. The most effective of the triple mutant variants is the specific molecule, T103N, N117Q, KHRR (296–299) AAAA t-PA (TNK t-PA).

EP 352.119 discloses Vampire Bat t-PA's (Bat-Pa (H), (I), and (L)). Vampire bat-Pa's are variants of native t-PA having a variety of sequence modifications. Although the Bat-Pa variants are structurally distinct from t-PA because they lack the Kringle 2 domain and plasmin-sensitive processing site, these variants are functionally similar to native t-PA. They are however, more potent than native t-PA.

Suzuki et al., *J. Cardiovasc. Pharmacal.* 22, 834–840 (1993) disclose t-PA variants in which a cysteine at position 84 of the growth factor domain of native t-PA is replaced by serine (C84S t-PA). Although this variant retains the functional activity of native t-PA, it has been shown to have a longer in vivo half life than native t-PA.

The 16-HETE may be administered alone or may be delivered in a mixture with other drugs, such as those disclosed above, for treating inflammatory or ischemic disease or condition. In some embodiments, a common administration vehicle (e.g., pill, tablet, implant, injectable solution, etc.) would contain both the 16-HETE useful in this invention and the therapeutic for treating inflammatory or ischemic disease or condition. Thus, the present invention also provides pharmaceutical compositions, for medical use, which comprise the 16-HETE of the invention together with one or more pharmaceutically acceptable carriers thereof and optionally other therapeutic ingredients.

When administered, the formulations of the invention are applied in pharmaceutically acceptable amounts and in pharmaceutically acceptable compositions. Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1–2% W/V); citric acid and a salt (1–3% W/V); boric acid and a salt (0.5–2.5% W/V); and phosphoric acid and a salt (0.8–2% W/V).

Suitable preservatives include benzalkonium chloride (0.003–0.03% W/V); chlorobutanol (0.3–0.9% W/V); parabens (0.01–0.25% W/V) and thimerosal (0.004–0.02% W/V).

Generally, daily oral doses of active compounds will be from about 0.01 milligrams/kg per day to 1000 milligrams/kg per day. It is expected that oral doses in the range of 50 to 500 milligrams/kg, in one or several administrations per day, will yield the desired results. Dosage may be adjusted appropriately to achieve desired drug levels, local or systemic, depending upon the mode of administration. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

A variety of administration routes are available. The particular mode selected will depend, of course, upon the particular combination of drugs selected, the severity of the condition mediated by neutrophil adhesion and/or neutrophil aggregation being treated, the condition of the patient, and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, topical, nasal, direct injection, transdermal, sublingual or other parenteral routes. The term "parenteral" includes subcutaneous, intravenous, intramuscular, or infusion. Intravenous and intramuscular routes are not particularly suited for long term therapy and prophylaxis. They could, however, be preferred in emergency situations such as a stroke or myocardial infarction. Direct injection could also be preferred for local delivery to the site of injury. Oral administration may be preferred for prophylactic treatment because of the convenience to the patient as well as the dosing schedule.

The compositions may conveniently be presented in unit dosage form and may be prepared by any of the methods well known in the art of pharmacy. All methods include the step of bringing the 16-HETE into association with a carrier which constitutes one or more accessory ingredients. In general, the compositions are prepared by uniformly and intimately bringing the 16-HETE into association with a liquid carrier, a finely divided solid carrier, or both, and then, if necessary, shaping the product.

Compositions suitable for parenteral administration conveniently comprise a sterile aqueous preparation of the 16-HETE, which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for oral, subcutaneous, intravenous, intramuscular, etc. can be found in Remington's Pharmaceutical Sciences, Mack Publishing Company, Easton, Pa.

Compositions suitable for oral administration may be presented as discrete units such as capsules, cachets, tablets, or lozenges, each containing a predetermined amount of the 16-HETE. Other compositions include suspensions in aqueous liquors or non-aqueous liquids such as a syrup, an elixir, or an emulsion.

Other delivery systems can include time-release, delayed release or sustained release delivery systems. Such systems can avoid repeated administrations of the 16-HETE of the invention, increasing convenience to the subject and the physician. Many types of release delivery systems are available and known to those of ordinary skill in the art. They include polymer based systems such as polylactic and polyglycolic acid, polyanhydrides and polycaprolactone; non-polymer systems that are lipids including sterols such as cholesterol, cholesterol esters and fatty acids or neutral fats such as mono-, di- and tri-glycerides; liposomes; phospholipids; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775 (Kent); 4,667,014 (Nestor et al.); and 4,748,034 and 5,239,660 (Leonard) and (b) diffusional systems in which an active component permeates at a controlled rate through a polymer, found in U.S. Pat. Nos. 3,832,253 (Higuchi et al.) and 3,854,480 (Zaffaroni). In addition, a pump-based hardware delivery system can be used, some of which are adapted for implantation.

Use of a long-term sustained release implant may be particularly suitable for treatment of chronic conditions mediated by neutrophil adhesion and/or neutrophil aggregation. "Long-term" release, as used herein, means that the implant is constructed and arranged to deliver therapeutic levels of the active ingredient for at least 7 days, and preferably 30–60 days. The implant may be positioned at the site of injury. Long-term sustained release implants are well known to those of ordinary skill in the art and include some of the release systems described above.

EXAMPLES

Example 1: Identification and Quantitative Analysis of Neutrophil Arachidonic Acid Metabolites Materials:

HETE standards (16(R)-, 16(S)-, 17-, 18-, 19- and 20-HETE) and 19-HETE-d$_3$ (99+atom % deuterium) were synthesized as described in Falck et al, *J Biol. Chem.* 265, 10244–10249 (1990). The standard lipoxygenase-derived HETEs (5-, 8-, 11-, 12-, and 15- HETE) were obtained from Biomol. Thrombin and fMLP were purchased from Parke-Davis (Morris Plains, N.J.). All solvents used were HPLC grade (Burdick and Jackson, Muskegon, Mich.) and other reagents were of the highest grade commercially available. BSTFA was purchased from Aldrich and [1-$^{14}$C] arachidonic acid (55 mCi/mmol) was purchased from du Pont Corp. (Wilmington, Del.). All other reagents were purchased from Sigma Chemical Co., St. Louis, Mo. unless otherwise noted.

Methods:

Preparation of human polymorphonuclear leukocytes. Venous blood (60–70 ml) was collected from four healthy, normal volunteers into syringes containing heparin (1 U/ml). Polymorphonuclear leukocytes (PMNs) were isolated by a histopaque density gradient technique as previously described in Liu et al., *Adhesion, Its role in Inflammatory Disease*, Freeman and Co., New York, 1992, pp 189–192. Briefly, blood aliquots (6 ml) were layered over two layers (3 ml) of histopaque 1077 and 1119 in a conical centrifuge tube. The sample was then subjected to centrifugation at 100×g for 30 minutes at room temperature and the top layer, containing the neutrophils, was carefully collected. Hypotonic lysis was used to separate out the red blood cells. The neutrophils were then isolated from the sample by centrifugation (2000×g) and suspended in Hanks balanced salt solution (HBSS) containing 1 mM Ca$^{2+}$ and 0.8 mM Mg$^{2+}$ for studies involving arachidonic acid metabolism, and in M199 (with 1% BSA) for neutrophil adhesion assays. Total cells were counted using a hemocytometer and leukocytes were counted after staining with Wright-Giemsa stain. For each experiment, the cell preparations used contain ≧97% neutrophils, having ≧95% viability as determined by a trypan blue exclusion assay.

Arachidonic acid metabolism. Neutrophils were suspended in HBSS (10$^7$ cells per ml) and allowed to stand for 10 minutes. Radioactively labeled arachidonic acid (1 to 50 µM) was produced with either a $^{14}$C label[containing 0.5 to 1 µCi [1-$^{14}$C]arachidonic acid/1 to 50 µM unlabeled arachidonic acid] or a deuterium label (1 unit arachidonic acid-d$_8$/2 units unlabeled arachidonic acid). The experimental samples were preincubated with inhibitors [SKF 525A (100 µM) or BW755C (94 µM) or indomethacin (10 µM)] for 10 minutes prior to the addition of arachidonic acid. At the end of the incubation, the labeled arachidonic acid, was added to the neutrophil suspension and allowed to incubate for 10 minutes at 37° C. A control sample was not subjected to preincubation with inhibitors.

After ten minutes in arachidonic acid the reaction was terminated by the addition of cold methanol (four volumes). The neutrophil methanol mixture was then subjected to acidification at pH 3.5 to 4 and the metabolite fraction was extracted with ethyl acetate. The extracts were washed with water and dried over anhydrous sodium sulfate. The metabolites were further purified by filtration to remove the sodium sulfate and evaporation to remove the ethyl acetate. The resultant residue was dissolved in methanol and injected on a reverse phase HPLC column (ODS silica, 250×4.6mm, Beckman). Eluate was collected at 1 ml/min. The solvent gradient was started at acetonitrile/water/acetic acid (62.5:37.5:0.1) and increased to 100% acetonitrile in 20 minutes. The effluent was passed through a UV detector (HP1050/ChemStation—Hewlett-Packard, Palo Alto, Calif.) and a radioactivity detector (Radiomatic, Meridian, Conn.) with a splitter (ratio 1:10) and collected in 1 ml fractions.

Gas chromatography/mass spectrometry: The fractions containing radioactive metabolites were evaporated under vacuum and derivatized as follows before being subjected to mass spectrometric analyses: Methyl esters were prepared with diazomethane solution in ether (100 μl, 3 min); Pentaflurobenzyl esters (PFB) were prepared with pentafluorobenzyl bromide and N,N-diisopropylethylamine as described Balazy, *J. Biol. Chem.*, 266, 23561–23567 (1991); and Trimethylsilyl (TMS) ethers of hydroxyl groups were prepared with N,O-bis (trimethylsilyl) trifluoroacetamide (BSTFA). The derivatives were then dissolved in isooctane and analyzed by GC/MS as describe below. In some experiments, aliquots of isooctane solution were mixed with catalytic amounts of 5% rhodium on alumina (Aldrich, Milwaukee, Wis.) in a microvial and bubbled with hydrogen gas at 0° C. for 5 min Balazy and Murphy *Anal. Chem.* 58, 1098–1100 (1986). The catalyst was precipitated by centrifugation and the reduced derivative was analyzed by GC/MS.

Aliquots (1 μl) were injected into a 15 m fused silica GC column (DB-1, 0.25 mm i.d., 0.25 μm film thickness, J and W Scientific, Folsom, Calif.) and eluted with a flow of helium (44 cm/s) and with a temperature program from 170° C. to 300° C. (rate 15° C./min). The mass spectrometer was operated in chemical ionization mode with negative ion detection (electron capture) using methane as a reagent gas (2.6 torr source pressure) or in electron ionization mode at 70 eV. The relative retention time of each derivative was expressed as carbon number equivalent calculated from retention times obtained for a series of methyl or PFB esters of saturated fatty acids ($C_{14}$–$C_{24}$) as described (Balazy, supra).

Quantitative analysis of 20-HETE and 16-HETE in neutrophil phospholipids Suspensions of human neutrophils (0.5 to 0.9×10$^8$ cells per ml) from three healthy donors not receiving medication were extracted using the Bligh and Dyer procedure as described Zhu et al., *Hypertension* 25, 854–859 (1995). The neutrophil total lipids containing 0.1 to 0.3 μmol of phosphorus, were treated with 200 μl of 0.1N potassium hydroxide/ethanol (1:1) or water/ethanol (in control experiments) for 1 hr at 50° C., and extracted with ethyl acetate after acidification (pH 3–4). Prior to extraction, internal standard, 19-HETE-$d_3$ (2 ng), was added. The extracts were dried and purified by RP-HPLC. Following derivatization with PFB bromide and BSTFA, the samples were analyzed by GC/MS as described (Zhu, supra). The amount of endogenous HETE was calculated from the standard curve prepared with 2 ng of 1 9-HETE-$d_3$ and 19-HETE (0.1 to 1 ng). The amount of phosphorus in the samples analyzed by GC/MS was determined spectrophotometrically (Zhu, supra).

Stereochemical analysis of 16-HETE The radiolabeled material in fraction 10, 16(R)-HETE, 16(S)-HETE and 20-HETE were separately esterified with pentafluorobenzyl bromide and the hydroxyl group was further esterified with α-naphthoyl chloride as described Laethem et al., *J. Biol. Chem.* 268, 12912–12918 (1993). The derivatives were purified by reverse-phase HPLC and analyzed on chiral-phase column (Pirkle type 1-A, 250×4.6 mm, Regis, Morton Grove, Ill.) and eluted with hexane containing 0.1% of isopropanol at 1 ml/min. The effluent was analyzed by a UV detector and collected in 0.2 ml fractions. The amount of radioactivity in these fractions was measured using scintillation counter.

Results:

Identification of neutrophil arachidonic acid metabolites Previously, Bednar et al. demonstrated that incubation of arachidonic acid with intact canine and human neutrophils produce polar metabolites whose formation can be inhibited by SKF525A or carbon monoxide (Bednar et al., *Biochem. Biophys. Res. Commun.* 123, 581–588 (1984); Bednar et al., *Biochem. Pharmacol.* 36, 1741–1747 (1987), and Kraemer, supra). These studies were later extended in human neutrophils. The latter studies revealed that intact neutrophils contain cytochrome P450 monooxygenase system and produce a cytochrome P450-dependent arachidonate metabolite which was found to inhibit neutrophil aggregation (Kraemer, supra; Bednar et al., *Biochem. Pharmacol.* 36;1741, 1987). The work of Hatzelmann and Ullrich (Hatzelmann, supra) showed that intact human neutrophils metabolize arachidonic acid into two major compounds: 20-HETE, an omega-hydroxylase product, and 15-HETE, a lipoxygenase product. Surprisingly the inventors of the present invention found that neither 20-HETE nor 15-HETE inhibited neutrophil aggregation (data not shown).

In order to identify the neutrophil arachidonic acid metabolites responsible for inhibiting neutrophil aggregation, human neutrophils were incubated with radio-labeled arachidonic acid. Incubations of arachidonic acid with human neutrophils resulted in formation of four radio-labeled products (metabolites A, B, C, and D). The major peak (D) contained unmodified arachidonic acid. Peaks B and C combined contained 5 to 8% of the total radioactivity injected and displayed absorbance at 234 nm, which is typical of conjugated double bonds. The material in peak A contained 10 to 15% of the radioactivity and it did not absorb UV light above 205 nm. Preincubation with inhibitors, established that the formation of product A by human neutrophils can be inhibited with SKF525A but not with BW755C suggesting that product A originated from metabolism mediated by cytochrome P450 monooxygenase, and not by lipoxygenase or cyclooxygenase.

Metabolite A was subjected to GC/MS analysis in order to further elucidate the components of metabolite A. The GC/MS analysis of metabolite A as a PFB, TMS derivative, with monitoring of ion m/z 391, which corresponded to a PFB ester, TMS ether derivative of a HETE molecule, produced an ion chromatogram which indicated the presence of two components at retention times of 7.33 min (component A1) and 8.01 min (component A2), having carbon number equivalents 20.9 and 22.4, respectively. Although variable amounts of metabolite A was isolated from neutrophils of each of the individual donors, the GC/MS analyses consistently yielded components A1 and A2 with a relative abundance of approximately 1 to 4. When deuterium-labeled arachidonic acid was included in the incubations, additional chromatographic peaks were observed (corresponding to ion m/z 399) which had retention times similar but slightly shorter than the non-labeled analogs, possibly as a result of the isotopic effect of the deuterium substitution.

The gas chromatographic mobility was compared with that of HETE standards. This comparison revealed that the component A2 coeluted with 20-HETE while the component A1, coeluted with 16-HETE. The PFB, TMS derivative of a standard sample of lipoxygenase HETEs (containing equal amount of 5-, 8-, 12-, and 15-HETE) eluted as a single peak at 7.45 min and did not coelute with either component of metabolite A or either of the 20- or 16-HETEs.

The electron capture spectra obtained for both the A1 and A2 components contained prominent ions at m/z 391 (M-181, loss of pentafluorobenzyl) and at m/z 301 (M-181-90, loss of pentafluorobenzyl and trimethylsilanol, SiMe$_3$OH) and were consistent with molecular weight of 320 amu for the metabolite having one hydroxyl group in the arachidonic acid structure. Inclusion of arachidonic acid-d$_8$ in the incubations produced a spectrum containing additional isotopic ion at m/z 399. When synthetic 16-HETE was mixed with metabolite A, only the intensity of component A1 increased and the added compound could not be separated from biologically derived A1, strongly indicating that Product A1 was 16-HETE. Catalytic reduction of PFB, TMS derivative resulted in a shift by 8 mass units producing a spectrum with ion m/z 399, typically observed for a HETE molecule with four double bonds reduced.

To further characterize these two components, the metabolite A was methylated, silylated with BSTFA and catalytically reduced with hydrogen. The electron ionization mass spectrometry of component A1 (carbon number equivalent 22.3) produced ions at m/z 399 (M—CH$_3$), m/z 357 and m/z 159 which originated from α-cleavage at C16, m/z 235 (m/z 357-32-90, loss of CH$_3$OH and SiMe$_3$OH). Fragment m/z 357 displayed a complex isotopic cluster of ions resulting from scrambling of deuterium during catalytic hydrogenation of isotopically-labeled molecule. Fragment ion m/z 328 originated from rearrangement of trimethylsilyl group to carboxylic group similar as observed for saturated hydroxy fatty acids. Eglinton et al., *Org. Mass. Spectrom.* 1, 593–611 (1968). The spectrum of synthetic, reduced 16-HETE, revealed the presence of these ions at retention time equivalent to carbon number 22.3 and was similar to the spectrum published by Falck et al. supra.

The stereochemistry of the hydroxyl at C16 in component A1 was established by chiral phase HPLC. The mixing of metabolite A with racemic synthetic 16-HETE followed by derivatization into 16-naphthoyl, PFB ester resulted in separation of this derivative into enantiomers and revealed that the radioactivity from biologically derived compound coeluted with the R isomer. The 20-naphthoyl, PFB derivative of 20-HETE was completely separated from the 16-HETE derivative during RP-HPLC purification prior to chiral analysis. These data were consistent with the structure of metabolite A1 as 16(R)-hydroxy-5,8,11,14-eicosatetraenoic acid formed by the action of cytochrome P450 on arachidonic acid assuming that the configuration of double bonds was unchanged from that of arachidonic acid. The electron ionization of the reduced molecule of component A2 as methyl ester TMS derivative (carbon number equivalent 23.5) revealed ions at m/z 414 (M$^+$), m/z 399 (M—CH$_3$), m/z 367 (M—CH$_3$—CH$_3$OH), m/z 324 (M—SiMe$_3$OH), m/z 292( M-32-90, loss of CH$_3$OH and SiMe$_3$OH), m/z 146 (SiMe$_3$O(CH$_2$)$_3$),CH$_3$) m/z 103 (Me$_3$Si—O=CH$_2$). The isotopic cluster of ions m/z 399 and 367 resulted from the scrambling of deuterium-labeled molecule during catalytic reduction of double bonds. This spectrum was consistent with reduced methyl ester, TMS ether derivative of a mixture of 20-HETE and 20-HETE-d$_8$.

Electron ionization of reduced metabolite B as methyl ester, TMS ether produced a spectrum (carbon number equivalent 21.8) which contained prominent ions at m/z 414 (M$^+$), 399 (M-15), 343 (α-cleavage at C15) and a base peak at m/z 173 (SiMe$_3$OCH(CH$_2$)$_4$CH$_3$). Ion m/z 343 displayed distinct isotopic cluster as expected for a reduced deuterium-labeled molecule. It was concluded that the metabolite B was 15-HETE.

The material in metabolite C contained at least two components absorbing UV light at 234 nm. The latter eluting component coeluted with standard 5-HETE. The material in peak C produced a complex mass spectrum indicative of 5-HETE and another unidentified product. Longer incubations of arachidonic acid with human neutrophils also resulted in formation of a polar compound identified as 20-carboxy arachidonic acid which originated from oxidative metabolism of 20-HETE.

Therefore, the mass spectrometric analyses of arachidonic acid metabolites produced by intact human neutrophils obtained from three human donors, revealed that a single monitoring of ion m/z 391, corresponding to a PFB, TMS derivative of a HETE molecule, consistently showed a minor, less polar component in addition to 20-HETE. Using mass spectrometric analysis and chiral analysis, it was revealed that the minor component was 16(R)-HETE, a product of cytochrome P450 and arachidonic acid which has not been previously observed in human PMN. Although, two recent studies provided mass spectrometric characterization (Hatzelmann, supra) and quantitation of 20-HETE in human PMNs (Hill, supra), 16-HETE was not observed. The lack of detection of 16-HETE is most likely due to the similar chromatographic mobility of 20-HETE and 16-HETE during RP-HPLC which results in the inability to observe separate peaks for these two HETEs using a low resolution of the radioactivity detector. It was also found in the present study that gas chromatographic conditions were capable of fully separating derivatives of unreduced 20-HETE from four subterminal HETEs. These chromatographic conditions were different than those described for isolation of 20-HETE from human neutrophils (Hatzelmann, supra, Hill, supra).

Example 2: 16-HETE and 20-HETE are Released from Neutrophil Phospholipids

Methods:

Quantitative analysis of 20-HETE and 16-HETE in neutrophilphospholipids was performed as described above in Example 1.

Results:

Release of endogenous 16-HETE and 20-HETE from neutrophil phospholipids When total lipid extracts from intact neutrophils were purified by HPLC and analyzed by electron capture GC/MS, no HETE molecules were detected by this GC/MS assay and therefore must be less than 10 pg per 10$^8$ cells. However, when neutrophil lipids were hydrolyzed with 0.1N potassium hydroxide, 20-HETE and 16-HETE were detected at a concentration of 341±69 pg per 10$^8$ cells and 10$^{8±26}$ pg per 10$^8$ cells respectively (Table 1).

TABLE 1

| Amounts of 16-HETE and 20-HETE released from intact human neutrophil phospholipids following alkaline hydrolysis | | |
|---|---|---|
| | 16-HETE (pg/10$^8$ cells) | 20-HETE (pg/10$^8$ cells) |
| control | n.d. | n.d. |
| Hydrolysis | 108 ± 26 | 341 ± 69 |

Average ± SEM of single measurements of neutrophil samples obtained from three donors. HETEs were measured by gas chromatography/mass spectrometry with 19-HETE-d$_3$ as an internal standard as described in the methods above.

Example 3: 16-HETE Inhibits Neutrophil Adhesion

Methods:

Synthesis of 16-HETE: Nucleophilic S$_N$2 addition of butyl magnesium bromide in Et$_2$O to the acetalic center of homochiral 1,3-dioxoian-4-one, prepared from 3-methyl-2-butenal and (R)-mandelic acid, followed by esterification with diazomethane readily afforded substituted O-allyl mandelate. Diisopropyl acetal was then obtained via low temperature ozonolysis, with $Me_2S$ workup and incubation of the resultant crude aldehyde with triisopropyl orthoformate in the presence of catalytic pyridinium p-toluenesulfonate (PPTS). Mild oxidative decarboxylation via an in situ-generated dioxetanone led to the corresponding benzoate. Minor amounts of free alcohol released during this process were benzoylylated and the combined degradation product was hydrolyzed, using trifluoracetic acid to furnish the aldehyde. Wittig condensation with 13-carbomethoxytrideca-3(Z), 6(Z), 9(Z)-trien-1-ylidene-triphenylphophorane and methanolysis of the benzoate produced methyl 16(S—OH—AA(8), $[\alpha]_D = -5.4$ (c 0.7, acetone). Mitsunobu inversion ($PhCO_2H, Ph_3P$, DEAD) and benozate removal (NaOMe, MeOH, 24° C., 2 h) yielded the 16(R)-isomer.

Neutrophil adhesion: Isolated neutrophils were resuspended in M199 containing 1% BSA with a final concentration of $3 \times 10^6$ cells per ml. Cells suspensions (1 ml) were incubated with or without a test compound, 16(S)-HETE, 16(R)-HETE, or 20-HETE (concentrations 1 nM to 10 µM) for 10 min and then placed into gelatin-coated wells and further incubated for 20 min at 37° C. The wells were washed three times with 0.5 ml of solution M199 to remove non-adherent cells. The adherent cells were then removed by addition of 0.4 ml of 0.25% trypsin-EDTA in 0.1M PBS to the gelatin-coated wells and incubation for 10 min at 37° C. The incubates were transferred and the wells were washed with 0.1 ml of M199 solution. The amount of cells in combined solutions was counted. In some experiments, the adhesion of neutrophils was stimulated by addition of 1 U/ml of thrombin to neutrophil suspension immediately prior to the transfer of cells to the wells. Experiments were performed in duplicates for each concentration of HETE. The inhibition of adhesion was expressed as percent of cells remaining in suspension (non-adherent) relative to control. The range of adherent PMNs in control incubations was 6 to 23%. This was increased two-fold in the presence of thrombin.

Neutrophil activity. Stimulated neutrophil aggregation and oxygen free radical release were examined in whole human blood using a whole-blood aggregometer-chemiluminometer (Chronolog, Haverton, Pa.) as described Bednar et al. *J Thromb. Thrombol.* 1, 179–185 (1995). Blood samples containing heparin (1 U/ml) as the anticoagulant were diluted in HBSS in proportion 1 to 9. Diluted blood aliquots (1 ml) were stirred (400 rpm) in a prewarmed (37° C.) siliconized cuvette containing cytochalasin b (5 µg/ml) and luminol (in 8 µl DMSO, 500 µM final concentration) and the test HETE (concentration 0.01 to 10 µM) for 10 min. Neutrophils were stimulated with a submaximal dose of fMLP ($5 \times 10^{-7}$M final concentration). The aggregation and chemiluminescence were simultaneously measured as changes of impedance and luminescence, respectively. The fMLP-induced chemiluminescence was calculated as the peak height of the reaction.

Figure 2:
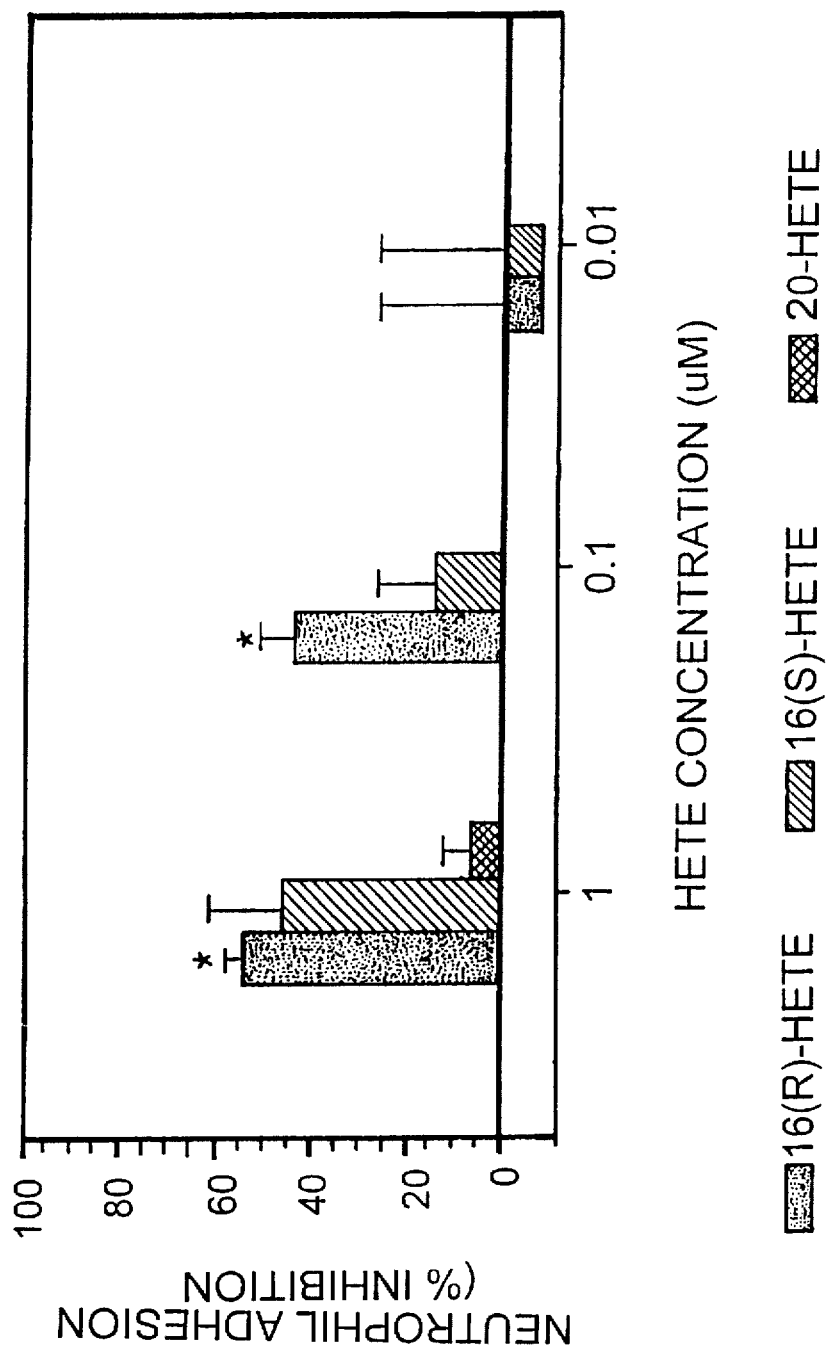
FIG. 2 is a bar graph depicting the percent inhibition of neutrophil adhesion to a gelatin matrix in response to a 10 minute pre-incubation with 16(R)-HETE, 16(S)-HETE, and 20-HETE on thrombin-stimulated human neutrophils.

Results:

Neutrophil-inhibitory activity of 16-HETE In order to determine the biological effects of 16-HETE on human neutrophils, neutrophil adhesion was analyzed after preincubation of 16-HETE and 20-HETE. At concentrations <20 µM, 16-HETE (R or S) and 20-HETE had no detectable agonist activity on human neutrophils. However, both stereoisomers of 16-HETE inhibited basal (FIG. 1) and thrombin-stimulated (FIG. 2) neutrophil adhesion to gelatin matrix. Treatment of neutrophils with 16(R)-HETE or 16(S)-HETE at concentrations from $10^{-8}$ to $10^{-5}$M inhibited neutrophil adhesion in a dose-dependent manner. The 16(R)-HETE at a concentration of 1 µM significantly (p<0.05) inhibited basal neutrophil adhesion by 73±11% and thrombin-stimulated adhesion (1 U/ml, $3 \times 10^6$ cells/ml) by 50±4%. In contrast to the 16(R)-HETE, the 16(S)-HETE was less potent in inhibiting unstimulated (39±8%) and thrombin-stimulated (40±14% inhibition) neutrophil adhesion at a concentration of 1 µM, although it exhibited the same biological activity as 16(R)-HETE. Preincubation of neutrophils with 10 µM of 16(R)-HETE completely inhibited neutrophil adhesion to gelatin. 20-HETE at concentrations $\leq 10$ µM did not inhibit neutrophil adhesion under either basal or stimulated conditions.

The 16(R)-HETE also inhibited fMLP-induced neutrophil aggregation (Table 2) with $IC_{50}$ of 1.2 µM. The 16(S)-HETE and 20-HETE were not active at concentrations of $\leq 10$ µM. Finally, the fMLP-stimulated release of oxygen free radicals was not inhibited by any of the three HETEs tested at concentrations $\leq 10$ µM (Table 2).

TABLE 2

The effect of preincubation with 16(R)-HETE, 16(S)-HETE and 20-HETE on neutrophil aggregation and oxygen free radicals (OFR) release stimulated by fMLP ($5 \times 10^{-7}$M, final concentration) in diluted human blood

|  | Aggregation | OFR Release |
| --- | --- | --- |
| 16(R)-HETE | 42.0 ± 11.0* | 8.9 ± 5.1 |
| 16(S)-HETE | 7.0 ± 3.5 | 5.6 ± 16.7 |
| 20-HETE | 8.1 ± 2.6 | 3.9 ± 13.4 |

Values represent percent of inhibition from HETE untreated cells (N = 3 to 4 in each group). 1 µM concentrations of HETE was used for each analysis. OFR release was measured by chemiluminescence as described above. *(p < 0.05)

The biological effects of 16-HETE on human neutrophils have not been previously reported. 16(R)-HETE displayed a potent inhibitory activity towards unstimulated and stimulated neutrophils. The biological effect observed with 16(R)-HETE was more potent than the effect observed with the opposite stereoisomer, 16(S)-HETE. 16(R)-HETE inhibited neutrophil adhesion, basal and thrombin-stimulated, and fMLP-induced neutrophil aggregation.

It was observed that in order to inhibit the adhesion of neutrophils to a gelatin matrix, a 10 min preincubation with 16(R)-HETE was required. This could reflect the time necessary for the 16-HETE to achieve membrane concentration sufficient for inhibition of adhesion. While not intending to be bound by any particular theory, the data presented above suggest that 16-HETE inhibits neutrophil activation indirectly, through induction of changes in phospholipid membrane, possibly via incorporation into sn-2 position of lyso-phospholipids. The results presented here clearly demonstrate that neutrophil lipids contain detectable quantities of 16-HETE and 20-HETE which must originate from endogenous arachidonic acid and exist as preformed cellular components in a form sensitive to alkaline hydrolysis.

In summary we have shown that 16(R)-HETE is formed in human neutrophils from arachidonic acid, it is an endogenous compound, and it has potent anti-adhesion and anti-aggregatory properties. These observations indicate that 16-HETE is an important effector in regulating the physiological response to human neutrophil activation.

Each of the foregoing patents, patent applications and references that are recited in this application are herein incorporated in their entirety by reference. Having described the presently preferred embodiments, and in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

We claim:

1. A method for treating a subject having an adverse medical condition mediated by neutrophil adhesion and/or neutrophil aggregation, said method comprising the step of:
administering to said subject having an adverse medical condition mediated by neutrophil adhesion and/or neutrophil aggregation 16-hydroxyeicosatetraenoic acid in an amount effective to inhibit neutrophil adhesion and/or neutrophil aggregation.

2. The method as recited in claim 1 wherein the adverse medical condition mediated by neutrophil adhesion and/or neutrophil aggregation is an inflammatory condition.

3. The method as recited in claim 2, wherein the inflammatory condition is meningitis.

4. The method as recited in claim 2, wherein the inflammatory condition is cerebral edema.

5. The method as recited in claim 2, wherein the inflammatory condition is arthritis.

6. The method as recited in claim 2, wherein the inflammatory condition is nephritis.

7. The method as recited in claim 2, wherein the inflammatory condition is adult respiratory distress syndrome.

8. The method as recited in claim 2, wherein the inflammatory condition is pancreatitis.

9. The method as recited in claim 2, wherein the inflammatory condition is myositis.

10. The method as recited in claim 2, wherein the inflammatory condition is neuritis.

11. The method as recited in claim 2, wherein the inflammatory condition is connective tissue disease.

12. The method as recited in claim 2, wherein the inflammatory condition is phlebitis.

13. The method as recited in claim 2, wherein the inflammatory condition is arteritis.

14. The method as recited in claim 2, wherein the inflammatory condition is vasculitis.

15. The method as recited in claim 2, wherein the inflammatory condition is allergy.

16. The method as recited in claim 2, wherein the inflammatory condition is anaphylaxis.

17. The method as recited in claim 2, wherein the inflammatory condition is gout.

18. The method as recited in claim 2, wherein the inflammatory condition is ulcerative colitis.

19. The method as recited in claim 2, wherein the inflammatory condition is ehrlichiosis.

20. The method as recited in claim 1, wherein the adverse medical condition mediated by neutrophil adhesion and/or neutrophil aggregation is an ischemic condition.

21. The method as recited in claim 20, wherein the ischemic condition is selected from the group consisting of a stroke and a myocardial infarction.

22. The method as recited in claim 21, further comprising administering a thrombolytic agent.

23. The method as recited in claim 1, wherein the 16-hydroxyeicosatetraenoic acid is administered orally.

24. The method as recited in claim 1, wherein the 16-hydroxyeicosatetraenoic acid is administered by direct injection.

25. The method as recited in claim 2, further comprising the step of administering to the subject a therapeutic agent other than and in addition to 16-hydroxyeicosatetraenoic acid for treating the inflammatory condition.

26. A pharmaceutical preparation comprising 16-hydroxyeicosatetraenoic acid and a pharmaceutically acceptable carrier.

27. The pharmaceutical preparation as in claim 26, further comprising a therapeutic agent other than and in addition to 16-hydroxyeicosatetraenoic acid for treating an ischemic condition.

28. The pharmaceutical preparation as in claim 27, wherein the therapeutic agent for treating the ischemic condition is selected from the group consisting of anticoagulation agents, antiplatelet agents, and thrombolytic agents.

29. The pharmaceutical preparation as in claim 27, wherein the therapeutic agent for treating the ischemic condition is an anticoagulation agent selected from the group consisting of heparin, warfarin, coumadin, dicumarol, phenprocoumon, acenocoumarol, ethyl biscoumacetate, and indandione derivatives.

30. The pharmaceutical preparation as in claim 27, wherein the therapeutic agent for treating the ischemic condition is an antiplatelet agent selected from the group consisting of aspirin, thienopyridine derivatives such as ticlopodine and clopidogrel, dipyridamole, R6D mimetic, and sulfinpyrazone.

31. The pharmaceutical preparation as in claim 27, wherein the therapeutic agent for treating the ischemic condition is a thrombolytic agent selected from the group consisting of plasminogen, ($\alpha_2$-antiplasmin, streptokinase, antistreplase, tissue plasminogen activator, urokinase, TNK t-PA, fibrolase, Bat-Pa (H), Bat-Pa (I), and Bat-Pa (L).

32. The pharmaceutical preparation as in claim 27, wherein the therapeutic agent for treating the ischemic condition is an anti-thrombin agent.

33. The pharmaceutical preparation as in claim 26, further comprising a therapeutic agent other than and in addition to 16-hydroxyeicosatetraenoic acid for treating an inflammatory condition.

34. The pharmaceutical preparation as in claim 33, wherein the therapeutic agent for treating the inflammatory condition is selected from the group consisting of antipathogen agents and antiphlogistics.

35. The pharmaceutical preparation as in claim 33, wherein the therapeutic agent for treating the inflammatory condition is an antibiotic selected from the group consisting of tetracycline antibiotics, aminoglysodes, macrolides, lincomycins, penicillanic acid (6-APA)-derivatives having 6β-acylamino groups, cephalosporanic acid (7-ACA)-derivatives having 7β-acylamino groups, penicillanic acid, β-lactam antibiotics of the clavam, penem and carbapenen type, and antibiotics of the bicozamycin, novobiocin, chloramphenicol or thiamphenicol, rifampicin, fosfomycin, colistin and vancomycin type.

36. The pharmaceutical preparation as in claim 33, wherein the therapeutic agent for treating the inflammatory condition is an antiphlogistic agent selected from the group consisting of glucocorticoids, immunosuppressive agents, penicillamine, hydroxychloroquine, and nonsteroidal inflammation-inhibitors.

37. The pharmaceutical preparation as in claim 33, wherein the therapeutic agent for treating the inflammatory condition is an antioxidant selected from the group consisting of superoxide dismutase, 21 aminosteroids/amino chromans, vitamin C, and vitamin E.

38. The pharmaceutical preparation as in claim 26, wherein the 16-hydroxyeicosatetraenoic acid is a substantially pure preparation of isolated 16-hydroxyeicosatetraenoic acid.

39. The pharmaceutical preparation as in claim 26, wherein the 16-hydroxyeicosatetraenoic acid is a synthetic preparation of 16-hydroxyeicosatetraenoic acid.

40. The pharmaceutical preparation as in claim 26, wherein the 16-hydroxyeicosatetraenoic acid is selected from the group consisting of 16(R)-hydroxyeicosatetraenoic acid and 16(S)-hydroxyeicosatetraenoic acid.

41. The pharmaceutical preparation of claims 26–40, wherein the 16-hydroxyeicosatetraenoic acid is substantially pure, isolated 16(R)-hydroxyeicosatetraenoic acid.

42. The pharmaceutical preparation as in claim 26, wherein the pharmaceutical preparation is an oral preparation.

43. The pharmaceutical preparation as in claim 26, wherein the pharmaceutical preparation is a parenteral preparation.

44. A pharmaceutical preparation consisting essentially of 16(R)-hydroxyeicosatetraenoic acid.

\* \* \* \* \*

UNITED STATES PATENT AND TRADEMARK OFFICE
CERTIFICATE OF CORRECTION

PATENT NO. : 5,753,702
DATED : 5-19-98
INVENTOR(S) : Bednar, et al.

It is certified that error appears in the above-identified patent and that said Letters Patent is hereby corrected as shown below:

On the title page insert the following :

U. S. PATENT DOCUMENTS

| EXAMINER INITIAL | | PATENT NUMBER | | | | | | | ISSUE DATE | PATENTEE | CLASS | SUBCLASS | FILING DATE IF APPROPRIATE |
|---|---|---|---|---|---|---|---|---|---|---|---|---|---|
| | | 5 | 5 | 2 | 7 | 8 | 9 | 0 | 06/18/96 | Rao, et al. | | | |
| | | 5 | 3 | 3 | 4 | 7 | 3 | 6 | 08/02/94 | Sun, et al. | | | |
| | | 5 | 1 | 6 | 4 | 3 | 8 | 1 | 11/17/92 | Wachter, et al. | | | |
| | | | | | | | | | | | | | |

FOREIGN PATENT DOCUMENTS

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | PC | T/U | S97 | /0 | 8 | 86 | 65 | 05/22/97 | International Search Report | | | | |
| | | | | | | | | | | | | | | |

OTHER DOCUMENTS

| | Knickle, L., et al., "Bioactivation of arachidonic acid by the cytochrome P 450...." |
|---|---|
| | Mol. Pharmacol., 1994, 45:6: 1273-80, ABSTRACT |
| | |

Signed and Sealed this

Fourth Day of May, 1999

Attest:

Attesting Officer

Q. TODD DICKINSON

Acting Commissioner of Patents and Trademarks

UNITED STATES PATENT AND TRADEMARK OFFICE
CERTIFICATE OF CORRECTION

PATENT NO. : 5,753,702
DATED : May 19, 1998
INVENTOR(S) : Bednar et al.

It is certified that error appears in the above-identified patent and that said Letters Patent is hereby corrected as shown below:

Column 1,
Line 3, between the "ARACHIDONIC ACID METABOLITE, 16-HETE" title and the "BACKGROUND OF THE INVENTION" paragraph, insert

-- GOVERNMENT SUPPORT

The invention was developed at least in part using Federal Funding under a grant from the National Institutes of Health under Grant Number NS31008 and NS28708. Accordingly, the government may have rights in the invention. --

Signed and Sealed this

Fourth Day of February, 2003

JAMES E. ROGAN
*Director of the United States Patent and Trademark Office*